United States Patent [19]

Christensen

[11] Patent Number: Plant 6,813

[45] Date of Patent: May 23, 1989

[54] HYBRID TEA ROSE PLANT CV. AROCORE

[75] Inventor: Jack E. Christensen, Ontario, Calif.

[73] Assignee: Bear Creek Gardens, Inc., Medford, Oreg.

[21] Appl. No.: 126,960

[22] Filed: Nov. 30, 1987

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Majestic, Parsons, Siebert & Hsue

[57] ABSTRACT

This invention relates to a new and distinct variety of hybrid tea rose plant cv. Arocore, particularly suited for garden decoration, identified by its dark red flower buds, and long-lasting medium red blooms having ruffled petals.

1 Drawing Sheet

The present invention relates to a new and distinct variety (cv. Arocore) of rose plant of the hybrid tea class. The plant is a moderately tall, bushy, hardy outdoor seedling cultivated for garden decoration. It was first originated by Jack E. Christensen in Ontario, Calif., U.S.A. under conditions of careful control and observation, and has as its seed parent the floribunda rose, Merci (U.S. Plant Pat. No. 3,144), and as its pollen parent, the hybrid tea rose Pharoah (U.S. Plant Pat. No. 2,859).

The new rose cv. Arocore is particularly distinguishable from other commercialized rose cultivars by the following combination of characteristics: its upright-spreading and vigorous growing plants of average height; its abundant dark red flower buds, borne on long strong stems; its dark red open blooms comprised of long-lasting, ruffled petals; its slight fruity fragrance; and its above average disease resistance and cold hardiness.

Arocore holds its distinguishing characteristics through succeeding propagations by budding and cuttings.

The new variety cv. Arocore may be distinguished from its seed parent, Merci, by the following combination of characteristics: Whereas Merci is a floribunda rose, Arocore is a hybrid tea rose. The petal color of Arocore is dark red, whereas the petal color of Merci is a medium-red.

The new variety may be distinguished from its pollen parent, Pharoah, by the following combination of characteristics: Whereas the flower color of Pharoah is bright orange red, the flower color of Arocore is dark red.

The accompanying drawing illustrates the new variety in color as grown in Somis, Calif., and shows the flowering thereof from bud to full bloom.

The descriptive matter which follows pertains to roses of the new variety grown outdoors in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety usually bears a single flower per a stem. Flower stems are strong and of medium length for the class. Outdoors, the plant blooms very freely, abundantly and continuously during the growing season. Blooms have a slight to moderate fruity fragrance.

BUD

The peduncle is short to average in length for the class, of average caliper, strong and bending. The peduncle is moderately rough with numerous stipitate glands and few prickles. Bud color is near Yellow-Green 144A. Parts of the bud exposed to sunlight are near Red-Purple 59A in color.

Before the calyx breaks, the bud is average in size for the class, of average length, pointed and ovoid in form with a conspicuous neck. There are many foliaceous appendages and stipitate glands on the surface of the bud. The bud usually bears deeply serrate foliaceous parts, extending beyond the tip of the bud equal to ¾ or more the bud length.

As the calyx breaks, petals exposed to sunlight are near Red 46A in color; sepal color is near Green 141C and near Red-Purple 59A where exposed to the sun.

The inner surface of the sepals is lined with a fine wooly tomentum. Sepal margins are lined with stipitate glands, gland-tipped cilia and hairs.

As the first petal opens, buds are average in size for the class, average to long in length and pointed to ovoid in form. Color of the outside of the bud petals is a dark red, near Greyed-Purple 185A toward the top of the bud and a darker red, near Red-Purple 187B, on the lower two thirds of the bud. The inside surface of the bud petals is near Red-Purple 185A in color.

The bud opens up well and is not prevented from opening by cold, hot or dry weather.

BLOOM

The size of the bloom when fully open is average for the class, about 4 to about 4½ inches in diameter. Petalage is double, averaging from about 45 to about 48 petals arranged irregularly, plus 5 to 6 petaloids.

Blooms at one half open are somewhat low centered to flat-topped in form, with petals moderately to very cupped to ruffled. Petal edges are somewhat flat.

When fully open, the blooms are somewhat flat, with loosely cupped petals, and flat petal edges.

The petals are of moderate to heavy substance, of average thickness, and slightly velvety on the inside and outside surface. Outside petals are nearly round in shape, sometimes scalloped, the apices usually bearing 2 to 3 notches. Intermediate petals are nearly round to broadly obovate in shape with apices bearing zero to one notch. Inside petals are nearly round to broadly obovate, with rounded apices usually bearing zero to one notch.

Petal colors may be modified by being blotched or overlaid with other colors under certain seasonal conditions.

The following paragraph describes the color values observed in a newly opened flower from a plant of the new variety grown outdoors in Somis, Calif. in November of 1987.

The color of the outside surface of the outside petals is comprised of dark red blends of between near Red-Purple 187A and Red-Purple 187B. The inside surface of the outer petals is near Greyed-Purple 185A with a very small basel attachment zone of near Yellow 7A. The outside surface of the intermediate petals is near Greyed-Purple 185A. The inside surface of the intermediate petals is near Red 46A with a very small basel attachment zone near Yellow 7A. The outside surface of the inner petals is near Red 46A. The inside surface of the inner petal is near Red 46A with basel attachment zone near Yellow 7A.

The following paragraph describes the color values observed in a flower open for three days outdoors from a plant of the new variety in November, 1987 at Somis, Calif.

The color of the outside surface of the outside petals is near Greyed-Purple 185A. The inside surface of the outside petal is near Red 46A, with a small basel attachment zone near Yellow 7A in color. The color of the outside surface of the inside petal is near Red 46A. The color of the inside surface of the inside petal is near Red 46A with a small basal attachment zone near Yellow 7A.

The generally color effect of the newly opened flower is a rich, vibrant dark red, near Red 46A on the outer petals.

After being open three days, the general color effect of the flower is near Red 46A margined with a darker red.

Petals usually drop off cleanly and are not particularly affected by hot or dry weather.

Flowers grown in the month of September last from 4 to 5 days on a bush in the garden. Cut flowers from rose plants grown outdoors in September last from 5 to 6 days when kept at living room temperatures.

REPRODUCTIVE ORGANS

Stamens are few to average in number and are arranged irregularly about the pistils; a few may also be mixed with petaloids. Filaments are short to medium in length and most have medium to large sized anthers. Anthers open approximately all at once. Mature anthers are near Yellow-Orange 17B in color; immature anthers are near Yellow-Orange 17C in color. Pollen is produced in somewhat sparse quantities and is near Yellow-Orange 17B in color.

Pistils are average to many in number for the class (about 40). Styles are uneven, short to average to long in length, of average caliper, and are loosely bunched. Stigma color is near Yellow-Orange 15D. Ovaries are usually enclosed in the calyx and a few protrude from the calyx.

Particulars regarding hips, sepals and seeds are unknown, as the female reproductive organs are sterile in the Somis, Calif. locality where plants described herein were grown.

FOLIAGE

The compound leaves comprise 5 to 7 leaflets. Leaves are borne in abundant quantities and are of average size for the class. Leaves are somewhat leathery and are non-glossy. Leaflets are oval to ovate in shape, with acute apices; their bases are round and their margins are dentate.

The color of the upper surface of mature leaves is near Yellow-Green 147A. The under surface of the mature leaf is near Green 139D. The upper surface of the young leaves is near Yellow-Green 147A with Greyed-Red 59B blended into a few areas of the leaf surface. The under surface of young leaves is near Green 138B in color, blended with near Greyed-Red 60C.

The rachis is light to average in size. Its upper side is grooved with some stipitate glands on the edges. The underside is sparsely prickly.

Stipules are short to average in length for the class and narrow, having short to long points turning out at an angle of more than 45° and are slightly recurved toward the stem.

Plants of the new variety are above average in their resistance to mildew and blackspot as compared with other cultivars now in commerce when grown under comparable conditions at Somis, Calif.

GROWTH

Plants of the new variety are average to tall in height, upright-spreading and moderately branched in habit. Plant growth is vigorous. Canes are of average caliper for the class. The main stems are near Green 139D in color, streaked with near Greyed-Brown 199D. They bear several to many large thorns which are average to long for the class and hooked downward. The thorn base is of average length and is moderately broad. Large thorns are near Greyed-Brown 199B in color. There are several to many small prickles near Greyed-Brown 199B and no hairs.

Branches are near Green 139D in color; they bear several to many large thorns of average-length for the class. Large thorns are hooked slightly downward and have moderately short, narrow bases. Large thorns are near Greyed-Brown 199B in color. There are several to many small prickles near Greyed-Brown 199B in color. There are no hairs.

New shoots are near Green 144B in color with a reddish tint near Red-Purple 60A. New shoots bear several to many large thorns which are of average length for the class. Large thorns are hooked slightly downward and have moderately narrow bases of average length. Large thorns are near Greyed-Purple 185A in color. There are no small prickles and no hairs.

I claim:

1. A new and distinct variety of hybrid tea rose plant cv. Arocore, the parts thereof; and being particularly characterized by its upright-spreading and vigorous growing plants of average height; its abundant dark red flower buds, borne on long strong stems; its dark red open blooms comprised of long-lasting, ruffled petals; its slight fruity fragrance; and its above average disease resistance and cold hardiness, substantially as described and illustrated herein.

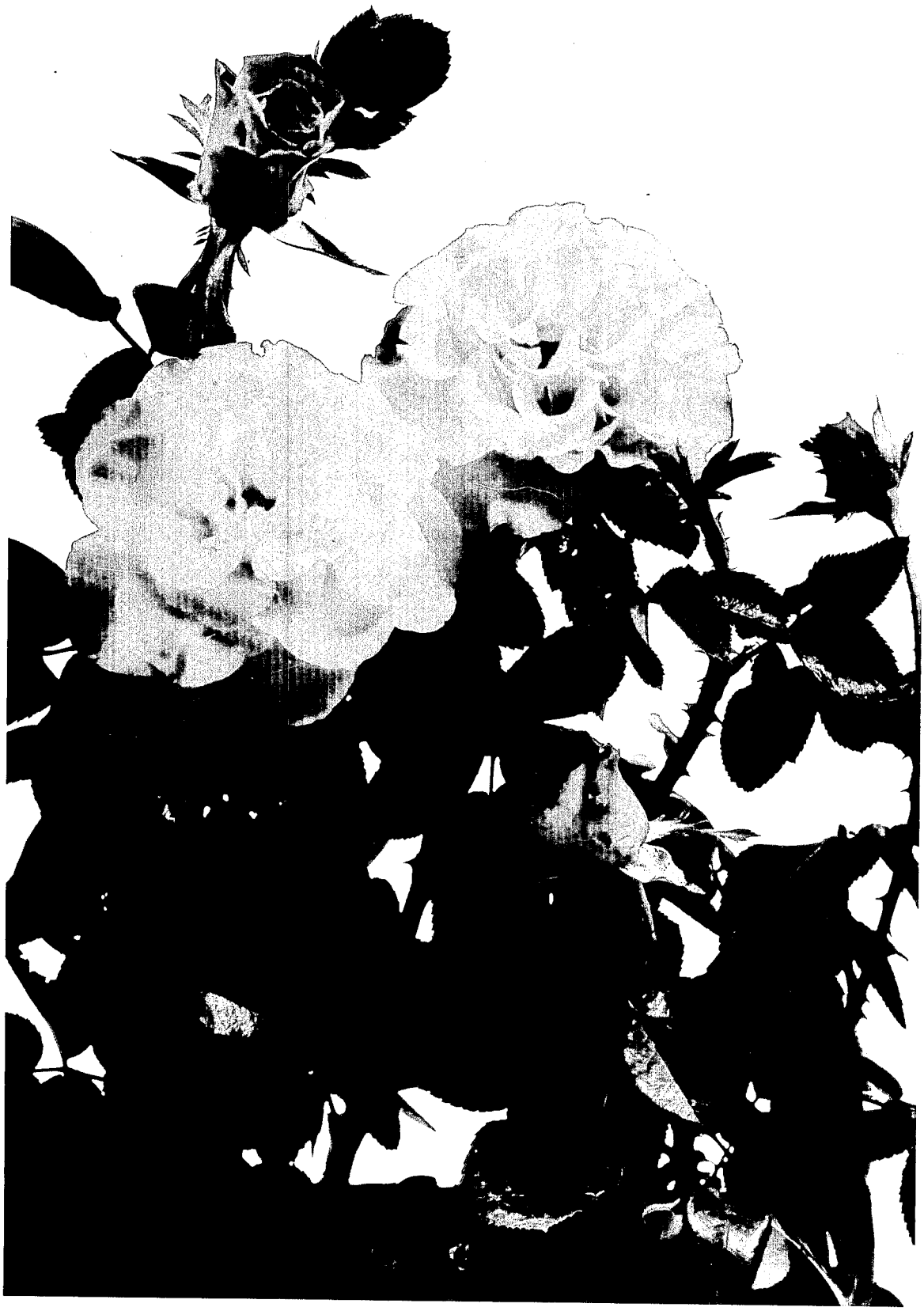

* * * * *